United States Patent
Talsma et al.

(10) Patent No.: US 10,299,999 B2
(45) Date of Patent: May 28, 2019

(54) FLAVOUR COMPOSITION COMPRISING MENTHOL AND MENTHANE CARBOXAMIDES

(71) Applicant: Givaudan, S.A., Vernier (CH)

(72) Inventors: Paul Alexander Talsma, Ashford Kent (GB); Tracy Bartholomew, Ashford Kent (GB)

(73) Assignee: Givaudan S.A., Vernier (CH)

( * ) Notice: Subject to any disclaimer, the term of this patent is extended or adjusted under 35 U.S.C. 154(b) by 19 days.

(21) Appl. No.: 15/206,866

(22) Filed: Jul. 11, 2016

(65) Prior Publication Data

US 2016/0317407 A1     Nov. 3, 2016

Related U.S. Application Data

(63) Continuation of application No. 13/980,760, filed as application No. PCT/EP2012/053082 on Feb. 23, 2012, now abandoned.

(30) Foreign Application Priority Data

Feb. 23, 2011 (GB) .................................. 1103103.6

(51) Int. Cl.
    *A23L 27/00*         (2016.01)
    *A61K 8/34*          (2006.01)
    *A61K 8/42*          (2006.01)
    *A61K 8/49*          (2006.01)
    *A61Q 11/00*        (2006.01)
    *A23L 27/20*         (2016.01)

(52) U.S. Cl.
    CPC ............. *A61K 8/34* (2013.01); *A23L 27/203* (2016.08); *A23L 27/205* (2016.08); *A23L 27/2054* (2016.08); *A61K 8/42* (2013.01); *A61K 8/4926* (2013.01); *A61Q 11/00* (2013.01); *A23V 2002/00* (2013.01); *A61K 2800/244* (2013.01); *A61K 2800/805* (2013.01); *A61K 2800/92* (2013.01)

(58) Field of Classification Search
    CPC .......... A61K 8/34; A61K 8/42; A61K 8/4926; A61K 2800/244; A61K 2800/805; A61K 2800/92; A23L 27/2054; A23L 27/205; A23L 27/203; A61Q 11/00; A23V 2002/00
    USPC ........ 426/533, 534, 535, 536, 537, 538, 650
    See application file for complete search history.

(56) References Cited

U.S. PATENT DOCUMENTS

| | | |
|---|---|---|
| 3,492,131 A | 1/1970 | Schlatter |
| 4,136,163 A | 1/1979 | Watson et al. |
| 4,150,052 A | 4/1979 | Watson et al. |
| 4,226,988 A | 10/1980 | Watson et al. |
| 4,248,859 A | 2/1981 | Rowsell et al. |
| 4,296,093 A | 10/1981 | Rowsell et al. |
| 4,318,900 A | 3/1982 | Rowsell et al. |
| 6,348,625 B1 | 2/2002 | Anderson |
| 6,399,614 B1 | 6/2002 | Leonardi et al. |
| 7,414,152 B2 | 8/2008 | Galopin et al. |
| 7,767,243 B2 | 8/2010 | Witkewitz et al. |
| 7,868,004 B2 | 1/2011 | Cole et al. |
| 8,242,289 B2 | 8/2012 | Oertling et al. |
| RE44,339 E | 7/2013 | Galopin et al. |
| 2005/0084447 A1 | 4/2005 | Wei |
| 2005/0159394 A1 | 7/2005 | Wei |
| 2005/0187211 A1 | 8/2005 | Wei |
| 2005/0207993 A1 | 9/2005 | Bazemore et al. |
| 2006/0051301 A1 | 3/2006 | Galopin et al. |
| 2006/0276667 A1 | 12/2006 | Galopin et al. |
| 2008/0112899 A1 | 5/2008 | Galopin et al. |
| 2008/0176945 A1 | 7/2008 | Galopin et al. |
| 2008/0305051 A1 | 12/2008 | Cole et al. |
| 2008/0319055 A1 | 12/2008 | Cole et al. |
| 2009/0054520 A1 | 2/2009 | Surburg et al. |
| 2009/0105237 A1 | 4/2009 | Bell et al. |
| 2010/0035938 A1 | 2/2010 | Bell et al. |
| 2010/0086498 A1 | 4/2010 | Haught et al. |
| 2010/0226864 A1 | 9/2010 | Oertling et al. |
| 2011/0091531 A1 | 4/2011 | Furrer et al. |
| 2012/0196018 A1 | 8/2012 | Villagran et al. |

FOREIGN PATENT DOCUMENTS

| | | |
|---|---|---|
| EP | 2 168 957 A2 | 3/2010 |
| GB | 233873 A | 5/1925 |
| GB | 1351761 A | 5/1974 |
| GB | 1351762 A | 5/1974 |
| GB | 1353381 A | 5/1974 |
| GB | 1421744 A | 1/1976 |
| GB | 1 457 671 A | 12/1976 |
| WO | WO 2004/089416 A1 | 10/2004 |
| WO | WO 2005/002582 A2 | 1/2005 |
| WO | WO 2005/015158 A1 | 2/2005 |
| WO | WO 2005/020897 A1 | 3/2005 |
| WO | WO 2005/049553 A1 | 6/2005 |
| WO | WO 2006/056087 A1 | 6/2006 |
| WO | WO 2006/056096 A1 | 6/2006 |
| WO | WO 2006/071749 A1 | 7/2006 |
| WO | WO 2006/092074 A1 | 9/2006 |
| WO | WO 2006/099762 A1 | 9/2006 |
| WO | WO 2006/125334 A1 | 11/2006 |

(Continued)

OTHER PUBLICATIONS http://www.leffingwell.com/MBE-SFC-Coolants.pdf, Apr. 2012.*

(Continued)

*Primary Examiner* — Leslie A Wong
(74) *Attorney, Agent, or Firm* — Curatolo Sidoti Co., LPA; Joseph G. Curatolo; Salvatore A. Sidoti

(57) ABSTRACT

The invention relates to flavor compositions comprising a mixture of coolant compounds comprising menthol and a menthane carboxamide selected from N-(4-cyanomethylphenyl) p-menthanecarboxamide, 2-isopropyl-5-methyl-N-(2-(pyridin-4-yl)ethyl)cyclohexanecarboxamide, or a mixture of N-(4-cyanomethylphenyl) p-menthanecarboxamide and 2-isopropyl-5-methyl-N-(2-(pyridin-4-yl)ethyl)cyclohexanecarboxamide, wherein the total amount of menthane carboxamide is about 0.1 to 10%.

20 Claims, No Drawings

(56) References Cited

FOREIGN PATENT DOCUMENTS

| WO | WO 2007/019719 A2 | 2/2007 |
| WO | WO 2009/0070910 | 6/2009 |
| WO | WO 2009/140783 A1 | 11/2009 |
| WO | WO 2010/059289 A1 | 5/2010 |
| WO | WO 2011/012671 A1 | 2/2011 |

OTHER PUBLICATIONS

Leffingwell, J. C., Cooling Ingredients and Their Mechanism of Action, 2009, Reprinted from Handbook of Cosmetic Science and Technology, 3rd ed., Barel et al.Eds., Informa Healthcare (Pub.), New York, http://www.leffingwell.com/download/Leffingwell%20-%20Handbook%20of%20Cosmetic%20Science%20and%20Technology.pdf.*

Watson H.R., et al., "New Compounds with the Menthol Cooling Effect," Journal of the Society of Cosmetic Chemists, New York, NY, US, vol. 29, No. 4, 1978, pp. 185-200.

Database Chemcats [Online], Chemical Abstracts Service, Columbus, Ohio, US; Jan. 12, 2005, XP002382088, retrieved from STN, order No. 6489078, abstract.

Database Chemcats, Chemical Abstracts Service, Columbus, Ohio, US; Jan. 18, 2005, XP002382089, order No. STK013323, abstract.

Database Chemcats, Chemical Abstracts Service, Columbus, Ohio, US; Jan. 18, 2005, XP002382090, order No. BAS 08858028, abstract.

Database Chemcats, Chemical Abstracts Service, Columbus, Ohio, US; Jan. 12, 2005, XP002382091, order No. 6383438, abstract.

Database Chemcats, Chemical Abstracts Service, Columbus, Ohio, US; Jan. 12, 2005, XP002382092; order No. 6399044, abstract.

Database Beilstein, Beilstein Institut zur Förderung der Chemischen Wlssenschaften; XP002382093 accession No. 3422960, abstract & Buu-Hoi: Z. Physiol. Chem, vol. 279, 1943.

Database Beilstein, Beilstein Institut zur Förderung der Chemischen Wissenschaften; XP002382094 accession No. 2328224, abstract & Inagaki, Shingaki: Chem. Lett., 1981.

Database Chemcats, Accession NR. 2004:1396439; ChemBridge Screening Library, Order NR. 5380996, Jan. 12, 2005, XP002384344, abstract.

Patani et al., Chemical Review, 1996, vol. 96, pp. 3147-3176.

PCT/EP2012/053082—International Search Report, dated Apr. 25, 2013.

PCT/EP2012/053082—International Written Opinion, dated Apr. 25, 2013.

PCT/EP2012/053082—International Preliminary Report on Patentability, dated Aug. 27, 2013.

GB 1103103.6—Search Report, dated Jun. 11, 2011.

Office Action in European Patent Application No. 12705673.7, dated Feb. 6, 2018.

Leffingwell, John C., "Cool without Menthol & Cooler than Menthol and Cooling Compounds as Insect Repellants," published Jun. 8, 2016, avaliable at http://www.lelfingwell.com/cooler_than_menthol.htm.

* cited by examiner

FLAVOUR COMPOSITION COMPRISING MENTHOL AND MENTHANE CARBOXAMIDES

The present application is a continuation of U.S. Ser. No. 13/980,760, now abandoned, having a 371(c) date of Aug. 15, 2013, which is a national stage application of International Application No. PCT/EP2012/053082, filed on Feb. 23, 2012, which claims priority from Great Britain Patent Application No. 1103103.6, filed Feb. 23, 2011, which applications are incorporated herein by reference.

The present invention is concerned with flavour compositions comprising menthol and menthane carboxamides, and in particular, with such compositions containing low levels of menthol. The invention is also concerned with consumable products, in particular oral care products, containing said flavour compositions.

A large number of coolant compounds of natural or synthetic origin have been described in the art. However, the most well-known compound is menthol, particularly 1-menthol, which is found naturally in peppermint oil, notably of *Mentha arvensis L* and *Mentha viridis L*. Of the isomers of menthol, the 1-isomer occurs most widely in nature and is typically what is referred by the name menthol having coolant properties. L-menthol has the characteristic peppermint odor, has a clean fresh taste and exerts a cooling sensation when applied to the skin and mucosal surfaces.

In order to deliver a strong consumer perception of freshness and cooling, flavours, in particular peppermint flavours, can exceed 50% by weight of menthol and it is not uncommon to find 60% or more.

However, despite it having gained very wide acceptance and use, menthol, when used alone, has an initial high flavour impact, but the flavour impact drops sharply within a few minutes after use and it tends to distort flavour notes and render the products containing it bitter. Furthermore, as well as bitterness problems, very high levels of menthol can restrict flavour creation and cause additional processing constraints.

In order to address some of the drawbacks of menthol use, it has become increasingly common to use it in admixture with other coolant compounds, most notably the N-substituted-p-menthane carboxamides. For example, GB233873 discloses such mixtures in order to provide different cooling profiles and even longer lasting coolant effects. Menthol-only formulations are compared with mixtures in which the amounts of menthol are reduced and replaced with like amounts of a menthane carboxamide coolant.

A challenge faced by the flavours industry today, is the drive from the consumer products companies to reduce the levels of non-active materials contained in their compositions. This is related, obviously to cost, but also to the need for sustainability, and the need to deliver greener products to the marketplace.

Accordingly, it is desirable to reduce the level of menthol without the loss of sensorial attributes and consumer liking attendant with its use. If one can reduce or compact the amount of a major component used in a flavour composition, one can, in turn, compact the amount of flavour composition used in consumer products, or alternatively one can exploit the use of lower levels of menthol to permit the use of more flavour ingredients thereby increasing a flavourist's latitude to create new and interesting flavour profiles and drive consumer preference. None of this would be possible, of course, if by reducing menthol one simply replaces it with other coolant materials in like amounts.

The applicant has now found that by employing certain menthane carboxamides in a flavour composition, it is possible to significantly reduced the amount of menthol conventionally employed in such compositions, whilst at the same time providing compositions having acceptable coolant and freshness effects, and which are favourably received by consumers in preference tests.

The invention provides in a first aspect a flavour composition comprising a mixture of coolant compounds consisting of menthol and a menthane carboxamide selected from N-(4-cyanomethylphenyl) p-menthanecarboxamide, 2-isopropyl-5-methyl-N-(2-(pyridin-4-yl)ethyl)cyclohexanecarboxamide, or a mixture of N-(4-cyanomethylphenyl) p-menthanecarboxamide and 2-isopropyl-5-methyl-N-(2-(pyridin-4-yl)ethyl)cyclohexanecarboxamide, wherein the total amount of menthane carboxamide is about 0.1 to 10%.

In a particular embodiment of the invention there is provided a flavour composition comprising a mixture of coolant compounds consisting of menthol and a menthane carboxamide selected from N-(4-cyanomethylphenyl) p-menthanecarboxamide, 2-isopropyl-5-methyl-N-(2-(pyridin-4-yl)ethyl)cyclohexanecarboxamide, or a mixture of N-(4-cyanomethylphenyl) p-menthanecarboxamide and 2-isopropyl-5-methyl-N-(2-(pyridin-4-yl)ethyl)cyclohexanecarboxamide, wherein the amount of menthol represents less than 70%, more particularly less than 50% by weight of the total flavour compositions and the total amount of menthane carboxamide is about 0.1 to 10%.

In a preferred embodiment of the invention, menthol is used in admixture with 2-isopropyl-5-methyl-N-(2-(pyridin-4-yl)ethyl)cyclohexanecarboxamide alone or in combination with N-(4-cyanomethylphenyl) p-menthanecarboxamide.

The total amount of menthol used in the flavour compositions of the present invention is an effective amount, when taken in conjunction with the menthane carboxamides, to provide a good cooling and breath freshening perception without bitterness. The exact amount of the menthol employed in the cooling compositions is a matter of preference subject to such factors as the degree of vapour action desired. Thus, the amount of menthol may be varied within the limits stated herein in order to obtain the result desired in the final product and such variations are within the capabilities of those skilled in the art without the need for undue experimentation.

In a particular embodiment of the invention the amount of menthol in the total flavour is about 1% to 50% by weight, still more particularly 5 to 30% by weight.

In a particular embodiment of the invention the total amount of menthane carboxamide in the total flavour is about 0.1 to 10% by weight, still more particularly 0.5 to 8% by weight.

In a particular embodiment the menthane carboxamide consists of N-(4-cyanomethylphenyl) p-menthanecarboxamide in an amount of 0.1 to 3% by weight in the total flavour, more particularly 0.5 to 2% by weight.

In yet another particular embodiment the menthane carboxamide consists of 2-isopropyl-5-methyl-N-(2-(pyridin-4-yl)ethyl)cyclohexanecarboxamide in an amount of 0.1 to 10% by weight, more particularly 0.5 to 7% by weight.

In yet another particular embodiment the menthane carboxamide consists of a mixture of N-(4-cyanomethylphenyl) p-menthanecarboxamide and 2-isopropyl-5-methyl-N-(2-(pyridin-4-yl)ethyl)cyclohexanecarboxamide, said mixture being provided in an amount of 0.1 to 13% by weight, more particularly 1 to 9% by weight of the total flavour composition.

In yet another particular aspect of the invention the mixture of N-(4-cyanomethylphenyl) p-menthanecarboxamide and 2-isopropyl-5-methyl-N-(2-(pyridin-4-yl)ethyl)cyclohexanecarboxamide is provided in a ratio of 1:100 to 30:1, more particularly 1:15 to 4:1.

The flavour compositions of the present invention surprisingly provided cooling and freshening effects that meet with high ratings in consumer preference testing despite reducing or compacting the amount of menthol and not replacing it with a similar amount of the menthane carboxamides. In other words, both menthol and the total coolant compounds are compacted. This result is indeed surprising as one cannot simply rationalise the finding on the basis that the menthane carboxamides are simply exerting a far greater cooling effect than menthol. The consumer preference tests do not merely reflect the intensity of cooling, indeed, if a coolant composition is too intense it can be offensive and unpleasant and rate poorly in consumer preference tests. Rather, the tests reflect an overall impression of liking and pleasantness.

Furthermore, particularly in consumer product compositions that are functional, such as oral care compositions, the coolant properties of a composition can act as a sensorial cue, informing the user of the compositions efficacy, and this can drive preference or liking for these types of products also. Both of the menthane carboxamides employed in the present invention exhibit a rather pronounced tingling sensation when applied to mucosal surfaces, particular the oral mucosa, which is particularly of interest in imparting this sensorial cue.

The invention provides in another of its aspects a method of compacting the amount of menthol employed in a flavour composition, comprising the step of adding to said flavour composition a mixture of menthol and menthane carboxamides as hereinabove defined.

The invention provides in yet another of its aspects a method of compacting the amount of coolant compounds employed in a flavour composition, comprising the step adding to said flavour composition a mixture of menthol and menthane carboxamides as hereinabove defined.

In a particular embodiment of the present invention there is provided a method of compacting the amount of menthol contained in a composition comprising the steps of:

I) screening the composition comprising menthol against a panel of consumers to determine a first preference score for said composition;

II) removing an amount of menthol from said composition and adding an amount of N-(4-cyanomethylphenyl) p-menthanecarboxamide, 2-isopropyl-5-methyl-N-(2-(pyridin-4-yl)ethyl)cyclohexanecarboxamide, or a mixture of N-(4-cyanomethylphenyl) p-menthanecarboxamide and 2-isopropyl-5-methyl-N-(2-(pyridin-4-yl)ethyl)cyclohexanecarboxamide, which amount added is lower than the amount of menthol removed on a weight basis, and subjecting it to a screening against a panel of consumers to obtain a second preference score that is higher than said first preference score.

The consumer test employed may be any of those test designs known and used by market researchers for determining preference or liking for taste of consumer products. For example, the test may be a Sequential Monadic evaluation of a pre-defined balanced Latin Square design wherein all products are tested by respondents. Further particulars of a suitable test are provided in the examples, below.

The menthane carboxamides as referred to above are described in International Publications WO 2005/049553 and WO 2007/019719.

The menthane carboxamides employed in the present invention contain asymmetric carbon atoms. Such diastereomeric mixtures can be separated into their individual diastereomers on the basis of their physical chemical differences by methods known per se, for example, by chromatography and/or fractional crystallization. Enantiomers can be separated by converting the enantiomeric mixtures into a diastereomric mixture by reaction with an appropriate optically active compound separating the diastereomers and converting the individual diastereomers to the corresponding pure enantiomers. All such isomers, including diastereomers mixtures and pure enantiomers are considered as part of the invention.

Particular examples of menthane carboxamides are the optical isomers shown below:

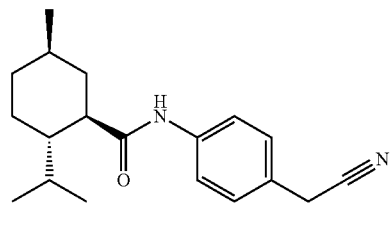

(1R,2S,5R)-N-(4-(cyanomethyl)-
phenyl)-2-isopropyl-5-methyl-
cyclohexanecarboxamide

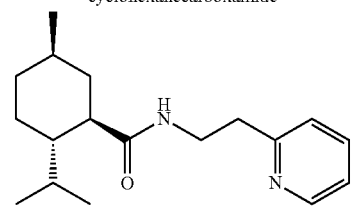

(1R,2S,5R)-2-isopropyl-5-methyl-
N-(2-(pyridin-2-yl)ethyl)-
cyclohexanecarboxamide The flavour compositions according to the invention may additionally comprise flavouring agents, sweetening agents and other auxiliaries commonly used in the formulation of such compositions.

Flavouring agents include but are not limited to:

natural flavors, artificial flavors, spices, seasonings, and the like. Exemplary flavoring agents include synthetic flavor oils and flavoring aromatics and/or oils, oleoresins, essences, distillates, and extracts derived from plants, leaves, flowers, fruits, and so forth, and a combination comprising at least one of the foregoing.

Exemplary flavor oils include spearmint oil, cinnamon oil, oil of wintergreen (methyl salicylate), peppermint oil, Japanese mint oil, clove oil, bay oil, anise oil, eucalyptus oil, thyme oil, cedar leaf oil, oil of nutmeg, allspice, oil of sage, mace, oil of bitter almonds, and cassia oil; useful flavoring agents include artificial, natural and synthetic fruit flavors such as vanilla, and citrus oils including lemon, orange, lime, grapefruit, yazu, sudachi, and fruit essences including apple, pear, peach, grape, blueberry, strawberry, raspberry, cherry, plum, prune, raisin, cola, guarana, neroli, pineapple, apricot, banana, melon, apricot, ume, cherry, raspberry, blackberry, tropical fruit, mango, mangosteen, pomegranate, papaya and so forth. Additional exemplary flavors imparted by a flavoring agent include a milk flavor, a butter flavor, a cheese flavor, a cream flavor, and a yogurt flavor; a vanilla flavor; tea or coffee flavors, such as a green tea flavor, an oolong tea flavor, a tea flavor, a cocoa flavor, a chocolate flavor, and a coffee flavor; mint flavors, such as a peppermint flavor, a spearmint flavor, and a Japanese mint flavor; spicy flavors, such as an asafetida flavor, an ajowan flavor, an anise flavor, an angelica flavor, a fennel flavor, an allspice flavor, a cinnamon flavor, a chamomile flavor, a mustard flavor, a cardamom flavor, a caraway flavor, a cumin flavor, a clove flavor, a pepper flavor, a coriander flavor, a sassafras flavor, a savory flavor, a Zanthoxyli Fructus flavor, a perilla flavor, a juniper berry flavor, a ginger flavor, a star anise flavor, a horseradish flavor, a thyme flavor, a tarragon flavor, a dill flavor, a *capsicum* flavor, a nutmeg flavor, a basil flavor, a marjoram flavor, a rosemary flavor, a bayleaf flavor, and a wasabi (Japanese horseradish) flavor; a nut flavor such as an almond flavor, a hazelnut flavor, a macadamia nut flavor, a peanut flavor, a pecan flavor, a pistachio flavor, and a walnut flavor; alcoholic flavors, such as a wine flavor, a whisky flavor, a brandy flavor, a rum flavor, a gin flavor, and a liqueur flavor; floral flavors; and vegetable flavors, such as an onion flavor, a garlic flavor, a cabbage flavor, a carrot flavor, a celery flavor, mushroom flavor, and a tomato flavor.

In some embodiments, other flavoring agents include aldehydes and esters such as cinnamyl acetate, cinnamaldehyde, citral diethylacetal, dihydrocarvyl acetate, eugenyl 49 formate, p-methylamisol, and so forth can be used. Further examples of aldehyde flavorings include acetaldehyde (apple), benzaldehyde (cherry, almond), anisic aldehyde (licorice, anise), cinnamic aldehyde (cinnamon), citral, i.e., alpha-citral (lemon, lime), neral, i.e., beta-citral (lemon, lime), decanal (orange, lemon), ethyl vanillin (vanilla, cream), heliotrope, i.e., piperonal (vanilla, cream), vanillin (vanilla, cream), alpha-amyl cinnamaldehyde (spicy fruity flavors), butyraldehyde (butter, cheese), valeraldehyde (butter, cheese), citronellal (modifies, many types), decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e., trans-2 (berry fruits), tolyl aldehyde (cherry, almond), veratraldehyde (vanilla), 2,6-dimethyl-5-heptenal, i.e., melonal (melon), 2,6-dimethyloctanal (green fruit), and 2-dodecenal (citrus, mandarin), and the like. Generally any flavoring or food additive such as those described in Chemicals Used in Food Processing, publication 1274, pages 63-258, by the National Academy of Sciences, can be used. This publication is incorporated herein by reference.

Some of the flavour ingredients useful in the present invention may contain menthol, for example peppermint oil. For the purpose of the present invention, the amounts of menthol referred to herein relate to the amounts of free menthol added to the flavour composition and it does not relate to any menthol that might be contained in a flavour ingredient, such as a flavour oil.

The amount of flavouring agents employed in the flavour formulation may typically be from about 1% to about 99%, and the particular amounts may vary depending on the nature of the flavour formulation created.

Sweetening agents include but are not limited:

high intensity sweetening agents. High intensity sweetening agents have a sweetness intensity substantially greater than that of sucrose. Suitable high intensity sweetening agents include water-soluble natural sweetening agents such as dihydrochalcones, monellin, *Stevia Rebaudiana* (steviosides), glycyrrhizin, and mixtures thereof. Suitable water-soluble artificial sweetening agents include saccharin and its soluble salts, i.e., sodium and calcium saccharin salts, cyclamate and its salts, 3,4-dihydro-6-methyl 1.2,3-oxathiazine4-one-2.2-dioxide (Acesulfame) and the sodium ammonium, and calcium salts thereof, and especially the potassium salt of 3,4-dihydro-6-methyl-1,2,3-oxathiazine4-one-2.2-dioxide (Acesulfame-K).

Suitable dipeptide based sweetening agents include L-aspartic acid derived sweetening agents such as L-aspartyl-L-phenvlalanine methyl ester (Aspartame), compounds described in U.S. Pat. No. 3,492,131, L-alpha aspartyl-N-(2,2,4,4-tetramethyl-3-thietanyl)-D-alaninamide hydrate (Alitame), methyl esters of L-aspartvl-L-phenylglycerine and L-aspartyl-L-2,5-dihvdrophenylglycine, Laspartyl-2.5-dihydro-L-phenyl-alanine, and L-aspartyl-L-(1-cyclohexen)alanine.

Other suitable water-soluble sweetening agents include those derived from naturally occurring water-soluble sweetening agents such as chlorinated derivatives of sucrose, e.g., chlorodeoxysugar derivatives such as derivatives of chlorodeoxysucrose and chlorodeoxy-galactosucrose. Examples of chlorodeoxysucrose and chlorodeoxygalactosucrose derivatives include but are not limited to 1-chloro-1'-deoxysucrose; 4-chloro-4-deoxy-alpha-D-galacto-pyranosyl-alpha-D-fructofuranoside, or 4-chloro-4-deoxygalactosucrose; 4-chloro-4-deoxy-alpha-D-galacto-pyranosyl-1-chloro-1 deoxy-beta-D-fructo-ftrranoside, or 4,1'-dichloro-4,1'dideoxygalactosucrose; 1',6'-dichloro-1',6'-dideoxysucrose; 4-chloro-4-deoxy-alpha-D-galacto-pyranosyl-1,6-dichloro-1,6-dideoxy-beta-D-fructo-furanoside, or 4,1',6'-trichloro-4, 1',6'-trideoxygalacto-sucrose; 4,6dichloro-4,6-dideoxy-alpha-D-galacto-pvranosvl-6-chloro-6-deoxy-beta-D-fructo-furanoside, or 4,6,6'-trichloro-4,6,6'-trideoxygalacto-sucrose, 6,1',6'-trichloro-6,1',6'-trideoxysucrose; 4,6-dichloro4,6-dideoxy-alpha-D-galacto-pvranosyl-1.6-dichloro-1,6-di-deoxy-beta-D-fructofuranoside, or 4,6,1',6'-tetrachloro-4,6,1',6'-tetradeoxygalacto-sucrose; and 4,6,1', 6'-tetrachloro4,6,1', 6'-tetradeoxy-sucrose. In a preferred embodiment, the chlorodeoxysugar derivative is 4,1',6' trichloro-4,1',6'-trideoxygalacto-sucrose, or 4-chloro 4-deoxy-alpha-D-galactopyranosyl-1,6dichloro 1,6dideoxy-beta-D-fructofuranoside, which is commercially available under the tradename Sucralose from McNeil Specialty Products Company, Skillman, N.J. Other suitable high intensity sweetening agents include protein based sweetening agents such as talin (*thaumaoccous danielli*, Thaumatin I and II).

The amount of sweetening agent employed in the flavour formulation may typically be from about 0.001% to about 1%, but greater or lesser amounts may be employed depending on the nature of the flavour formulation created.

Auxilliaries are materials used in flavour formulations for their attributes and properties other than their ability to impart flavour or sweetening effects. Auxilliaries include additives, surfactants, emulsifiers, superfatting agents, bodying agents, thickeners, polymers, silicone compounds, fats, waxes, stabilizers, preservatives, antioxidants, dyes, antimicrobial agents, solvents and co-solvents; viscosity and rheology modifiers; gelling agents; preservative materials such as fungicides and bactericides; pigments, dyestuffs and colouring matters; extenders, fillers and reinforcing agents; stabilisers against the detrimental effects of heat and light; bulking agents, which may include mineral adjuvants, which may serve as fillers and textural agents. Suitable mineral adjuvants include calcium carbonate, magnesium carbonate, alumina, aluminum hydroxide, aluminum silicate, talc, tricalcium phosphate, tricalcium phosphate and the like, which can serve as fillers and textural agents.

Additional bulking agents (carriers, extenders) suitable for use include sweetening agents such as monosaccharides, disaccharides, polysaccharides, sugar alcohols, polydextrose, and maltodextrins; minerals, such as calcium carbonate, talc, titanium dioxide, dicalcium phosphate; and combinations thereof.

Fillers modify the texture and aid processing. Examples of such fillers include magnesium and aluminum silicates, clay, alumina, talc, titanium oxide, cellulose polymers, and the like.

Other suitable and desirable additives are described in standard texts, such as "Handbook of Industrial Chemical Additives", ed. M. and I. Ash, 2nd Ed., (Synapse 2000).

The flavour compositions, or particular ingredients thereof may be provided in many distinct physical forms, for example solid, liquid or encapsulated forms. Selection of the particular form may be selected by reason of ease of handling or storage, or in order to achieve a particular effect such as sustained or controlled release. By "encapsulated form" is meant that a material or ingredient is contained within an encapsulating material, which protects and/or retains it and permits its release either gradually or completely. All known methods of encapsulation, may be used, for example, coacervation, spray drying, absorption into a porous substrate and the like. All possible encapsulation materials may also be used, for example, natural fibres, minerals of large surface area and polymeric materials.

The amount of flavour composition employed in a consumer product may vary according to the particular effect that is desired. Typically, however, the flavour composition may be used in an amount of about 0.01 to 2% by weight based on the weight of the consumer product, more particularly 0.1 to 1.5% by weight.

The flavour compositions according to the invention may be used in any manner of consumable products. By "consumable products" is meant any product intended to be applied to the body, or placed in the mouth before discarding (e.g. by rinsing) or ingesting, for the purpose of therapy, treatment, nourishment or enjoyment. Consumable products may be in any physical form such as creams, gels, lotions, alcoholic and aqueous/alcoholic solutions, emulsions, dispersions, stick preparations or the like.

Flavour compositions may be employed in consumable products for use in oral care.

In relation to consumable products, "oral care" relates to any product applied to the oral cavity for the purposes of cleaning, freshening, healing, deodorising the cavity or any part thereof. Such compositions include, but are not limited to, toothpastes, toothgels, tooth powders, tooth whitening products, mouthwashes, lozenges, dental floss, tooth picks, anti-plaque and anti-gingivitis compositions, throat lozenges, throat drops, inflammatory compositions, compositions for treatment of nasal symptoms, cold symptoms and upper gastrointestinal tract distress, compositions for cold relief, for alleviating discomfort of hot flash, gargle compositions.

Oral care products utilising these compounds may be prepared by blending a flavour composition with one or more of the conventional ingredients normally associated with such products, in standard quantities. Examples of such standard ingredients include, but are not limited to, *Mentha Arvensis, Mentha Piperita, Mentha Spicata, Mentha Cardiaca*, Synthetic Mints, Anethole, Methyl Salicylate, Eucalyptol, Cinnamic Aldehyde, Eugenol, Calcium Carbonate, Silica (Precipitates & Xerogels), Dicalcium Phosphate, Alumina, Sodium Lauryl Sulphate, Betaine, Glycerine, Sorbitol, Water, Saccharin, Sodium Cyclamate, Aspartame, Xylitol, Sodium Carboymethyl Cellulose, Methyl Cellulose, Sodium Carageenate, Xanthan Gum, Polyvinyl Pyrrolidone, Sodium Tripolyphosphate, Ethyl Alcohol, Sodium Fluoride, Sodium Monofluorophosphate, Stannous Fluoride, Potassium Citrate, Potassium Chloride, Potassium Nitrate, Strontium Acetate, Strontium Chloride, Sodium Tripolyphosphate, Cetyl Pyridinium Chloride, Hexetidine, Sanguinarine, Triclosan, Chlorhexidine, Zinc Citrate, Zinc Sulphate, Zinc Chloride, Calcium Glycerophosphate, Sodium Bicarbonate, Tetra Sodium Pyrophosphate, Tetra Potassium Pyrophosphate.

Some of these materials may be present in encapsulated form, as this term is described above.

The flavour compositions according to the invention may be used in personal care products such as pharmaceuticals, cosmetics and toiletries.

When used within cosmetics and toiletries, the formulations can be used in any of the "Reported Product Categories" listed by the Cosmetic, Toiletries and Fragrance Association's 'International Cosmetic Ingredient Dictionary and Handbook', and with any one or more of the ingredients cited as being used for the reported product categories.

The Reported Product Categories are: Aftershave lotions, Baby lotions, oils, powders and creams, Baby products miscellaneous, Baby shampoos, Basecoats and undercoats, Bath capsules, Bath oils, tablets and salts, Bath preparations miscellaneous, Bath soaps and detergents, Beard softeners, Blushers, Body and hand preparations, Bubble baths, Cleaning products, Colognes and toilet waters, Cuticle softeners, Dentifrices, Deodorants, Depilatories, Douches, Eye lotions, Eye makeup preparations miscellaneous, Eye makeup removers, Eye shadows, Eyebrow pencils, Eyeliners, Face and neck preparations, Face powders, Feminine hygiene deodorants, Foot powders and sprays, foundations, Fragrance preparations miscellaneous, Hair bleaches, Hair colour sprays, Hair colouring preparations miscellaneous, Hair conditioners, Hair dyes and colours, Hair lighteners with colour, Hair preparations, Hair rinses, Hair shampoos, Hair sprays, Hair straighteners, Hair tints, Hair wave sets, Indoor tanning preparations, Leg and body paints, Lipsticks, Makeup bases, Makeup fixatives, Makeup preparations, Manicuring preparations miscellaneous, Mascara, Men's talcum, Moisturising preparations, Mouthwashes and breath fresheners, Nail creams and lotions, Nail extenders, Nail polish and enamel removers, Nail polish and enamels, Night skin care preparations, Oral hygiene products miscellaneous, Paste masks, Perfumes, Permanent waves, Personal cleanliness products miscellaneous, Powders, Preshave lotions, Rouges, Sachets, Shampoos, Shaving cream, Shaving preparations miscellaneous, Shaving soap, Skin care preparations miscellaneous, Skin fresheners, Suntan gels, creams and liquids, Suntan preparations miscellaneous, Tonics, dressings and other hair grooming aids.

In the preparation of the abovementioned products, there may be used all or any of the standard Auxilliaries found in such products and described above, used in art-recognised quantities.

Other suitable and desirable additives or auxilliaries are described in standard texts, such as "Handbook of Industrial Chemical Additives", ed. M. and I. Ash, 2nd Ed., (Synapse 2000).

Further formulation details useful in association with these compounds may be found in standard texts, for example, "Handbook of Cosmetic Science and Technology", ed. Pays, Barel & Maibach, 2nd Ed. (Dekker, 2005).

Flavour compositions according to the invention may be used in foodstuffs of all kinds, confectionery, baked goods, sweet goods, dairy products and beverages.

The term "confectionery" includes, but is not limited to:

chewing gum (which includes sugarized gum, sugar-free gum, functional gum and bubble gum), center-fill confections, chocolate and other chocolate confectionery, medicated confectionery, lozenges, tablets, pastilles, mints, standard mints, power mints, chewy candies, hard candies, boiled candies, breath and other oral care films or strips, candy canes, lollipops, gummies, jellies, fudge, caramel, hard and soft panned goods, toffee, taffy, liquorice, gelatin candies, gum drops, jelly beans, nougats, fondants, or combinations of one or more of these, or edible compositions incorporating one or more of these.

The confectionery compositions can be incorporated into an otherwise conventional hard or soft confectionery format using standard techniques and equipment known to those of ordinary skill in the art. The confectionery compositions can also be center filled and/or coated with hard, soft, or particulate coatings.

The term "baked goods" includes, but is not limited to:

alfajores, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, The term "sweet goods" includes, but is not limited to:

breakfast cereals, ready-to-eat ("rte") cereals, family breakfast cereals, flakes, muesli, other rte cereals, children's breakfast cereals and hot cereals.

The term "dairy products" includes, but is not limited to:

ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners, powder milk, flavored powder milk drinks, cream, yoghurt, plain/natural yoghurt, flavored yoghurt, fruited yoghurt, probiotic yoghurt, drinking yoghurt, regular drinking yoghurt, probiotic drinking yoghurt, chilled and shelf-stable desserts, dairy-based desserts and soy-based desserts.

Other foodstuff includes, but is not limited to:

chilled snacks, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, uht soup, frozen soup, pasta, canned pasta, dried pasta, chilled/fresh pasta, noodles, plain noodles, instant noodles, cups/bowl instant noodles, pouch instant noodles, chilled noodles, snack noodles, dried food, dessert mixes, sauces, dressings and condiments, herbs and spices, spreads, jams and preserves, honey, chocolate spreads, nut-based spreads, and yeast-based spreads.

The term "beverage" as used herein means any drinkable liquid or semi-liquid, including for example:

flavored water, soft drinks, fruit drinks, coffee-based drinks, tea-based drinks, juice-based drinks (includes fruit and vegetable), milk-based drinks, gel drinks, carbonated or non-carbonated drinks, powdered drinks, alcoholic or non-alcoholic drinks.

In the preparation of the abovementioned products, there may be used all or any of the standard ingredients found in such products, used in art-recognised quantities. Examples of such ingredients include (but are by no means limited to) solvents and co-solvents; surfactants and emulsifiers; viscosity and rheology modifiers; thickening and gelling agents; preservative materials; pigments, dyestuffs and colouring matters; extenders, fillers and reinforcing agents; stabilisers against the detrimental effects of heat and light, bulking agents, flavoring and flavor-enhancing agents, warming agents, breath fresheners, mouth moisteners, coloring agents, acidulants, buffering agents and antioxidants.

With respect to chewing gum compositions in particular, suitable components include in addition to a water-insoluble gum base portion, a water soluble bulk portion and various additives. The water soluble portion may include sweetening agents, bulking agents, softening agents and/or plasticizers, waxes, emulsifiers, thickening agents, flavor enhancing agents, warming agents, breath fresheners, mouth moisteners, acidulants, coloring agents, buffering agents, antioxidants, nutraceuticals, medicaments and other conventional chewing gum additives that provide desired attributes. Other conventional chewing gum additives known to one having ordinary skill in the art may also be used in the water soluble bulk portion.

Softeners and plasticizers may be used to provide a variety of desirable textures and consistency properties. Suitable plasticizers and softeners may include lanolin, palmitic acid, oleic acid, stearic acid, sodium stearate, potassium stearate, glyceryl triacetate, glyceryl lecithin, glyceryl monostearate, propylene glycol monostearate, acetylated monoglyceride, glycerine, and a combination comprising at least one of the foregoing. Because of the low molecular weights of these softeners and plasticizers, they are able to penetrate the fundamental structure of the gum base, making it plastic and less viscous.

Waxes may be used in the gum base to soften the elastomer, improve the elasticity of the gum base, and obtain a variety of desirable textures and consistency properties. Suitable waxes may include natural and synthetic waxes, hydrogenated vegetable oils, petroleum waxes such as polyurethane waxes, polyethylene waxes, paraffin waxes, microcrystalline waxes, fatty waxes, sorbitan monostearate, tallow, and propylene glycol. Low melting waxes may be used in the gum compositions. These waxes typically have a melting point below about 60° C., and specifically about 45 to about 55° C. High melting waxes may also be used in the gum base. Such high melting waxes include beeswax, vegetable wax, candelilla wax, camauba wax, most petroleum waxes, and the like, and combinations thereof.

Suitable emulsifiers include distilled monoglycerides, acetic acid esters of mono and diglycerides, citric acid esters of mono and diglycerides, lactic acid esters of mono and diglycerides, mono and diglycerides, polyglycerol esters of fatty acids, ceteareth-20, polyglycerol polyricinoleate, propylene glycol esters of fatty acids, polyglyceryl laurate, glyceryl cocoate, gum arabic, acacia gum, sorbitan monostearates, sorbitan tristearates, sorbitan monolaurate, sorbitan monooleate, sodium stearoyl lactylates, calcium stearoyl lactylates, diacetyl tartaric acid esters of mono- and diglycerides, glyceryl tricaprylate-caprate/medium chain triglycerides, glyceryl dioleate, glyceryl oleate, glyceryl lacto esters of fatty acids, glyceryl lacto palmitate, glyceryl stearate, glyceryl laurate, glycerlyl di laurate, glyceryl monoricinoleate, triglyceryl monostearate, hexaglyceryl distearate, decaglyceryl monostearate, decaglyceryl dipalmitate, decaglyceryl monooleate, polyglyceryl 10 hexaoleate, medium chain triglycerides, caprylic/capric triglyceride, propylene glycol monostearate, polysorbate 20, polysorbate 40, polysorbate 60, polysorbate 80, polysorbate 65, hexylglyceryl distearate, triglyceryl monostearate, tweens, spans, stearoyl lactylates, calcium stearoyl-2-lactylate, sodium stearoyl-2-lactylate lecithin, ammonium phosphatide, sucrose esters of fatty acids, sucroglycerides, propane-1,2-diol esters of fatty acids, and combinations comprising at least one of the foregoing.

Suitable thickening agents include cellulose ethers (e.g., hydroxyethyl cellulose, hydroxypropylmethyl cellulose, or hydroxypropyl cellulose), methylcellulose, carboxymethylcellulose, and combinations thereof. Additional polymers useful as thickeners include carbomer, polyvinyl pyrrolidone, polyvinyl alcohol, sodium alginate, polyethylene glycol, natural gums like xanthan gum, tragacantha, guar gum, acacia gum, arabic gum, water-dispersible polyacrylates like polyacrylic acid, methyl methacrylate copolymer, and carboxyvinyl copolymers.

A chewing gum composition may additionally contain bulking agents and fillers, nutraceuticals, medicaments and flavoring agents, as hereinabove described.

The chewing gum composition may be coated or compressed, and be in the form of slabs, sticks, pellets, cubes, trapezoids, rectangles, or balls. The compositions of the different forms of the gum compositions will be similar but may vary with regard to the ratios of the ingredients. Center-filled gum is another common gum form, the center-fill is typically an aqueous liquid or gel, which is injected into the center of the gum during processing. The center-filled gum may also be optionally coated and may be prepared in various forms, such as in the form of a lollipop.

There now follows a series of examples that serve to illustrate the invention.

EXAMPLE 1

The following three flavours were prepared with propylene glycol as a diluent to make the flavours up to 100%:

|  | (A) % w/w | (B) % w/w | (C) % w/w |
| --- | --- | --- | --- |
| Peppermint Heart | 43.00 | 43.00 | 43.00 |
| Menthol | 50.00 | 10.00 | 10.00 |
| Propylene Glycol | 7.00 | 42.00 | 45.00 |
| Evercool 190 | — | 5.00 | — |
| Evercool 180 | — | — | 2.00 |

Evercool 190 = 2-isopropyl-5-methyl-N-(2-(pyridin-4-yl)ethyl)cyclohexanecarboxamide
Evercool 180 = N-(4-cyanomethylphenyl) p-menthanecarboxamide The Flavours were each incorporated into a standard silica toothpaste base at 1%:

|  | (1) % | (2) % | (3) % |
| --- | --- | --- | --- |
| Silica toothpaste base | 99.00 | 99.00 | 99.00 |
| Flavour A | 1.00 | — | — |
| Flavour B | — | 1.00 | — |
| Flavour C | — | — | 1.00 |

All three toothpastes were coded and given to 37 naive volunteers. The volunteers were asked to brush the teeth for 30 seconds and score each toothpaste (0-10 scale) for cooling, tingling and freshness at each of six time points: 0 minutes, 5 minutes, 10 minutes, 20 minutes, 30 minutes and 60 minutes. At the end of the 60 minutes, they were also asked for their overall preference scores (0-10 scale). The results are shown in FIGS. 1 through 4.

Flavour B, containing 10% added menthol and 5% Evercool 190, performed the best for cooling, tingling and freshness and was most preferred.

Flavour C, containing 10% added menthol and 2% Evercool 180, performed better than flavour A after 10 minutes and was the strongest performing at 60 minutes. This had similar overall preference to that of flavour A.

Low levels of Evercool 190 or Evercool 180 can replace high levels of menthol in a toothpaste flavour and still provide superior sensorial benefits and be preferred to the flavour with the high levels of menthol.

EXAMPLE 2

Two consumer acceptable flavours containing 74% and 63% added menthol respectively, had the added menthol removed and substituted with either Evercool 190 or Evercool 190 and Evercool 180.

|  | Flavour 1 | Flavour 2 | Flavour 1 Mod | Flavour 2 Mod |
| --- | --- | --- | --- | --- |
| Peppermint Heart (Flavour 1) | 26% |  | 26% |  |
| Peppermint Heart (Flavour 2) |  | 37% |  | 37% |
| Menthol | 74% | 63% |  |  |
| Evercool 190 |  |  | 4% | 4% |
| Evercool 180 |  |  |  | 1.2% |

The flavours were dosed into typical silica toothpaste according to the following, such that the modified flavours were dosed at a lower, compacted level:

| Flavour 1 | 1.20% |
| --- | --- |
| Flavour 2 | 1.00% |
| Flavour 1 mod | 0.37% |
| Flavour 2 mod | 0.42% |

The two sets of samples were coded and given to 16 naïve volunteers who were asked to brush their teeth for 30 seconds and score (0-10 scale) for cooling, freshness and tingling at 0 minutes, 5 minutes, 10 minutes, 20 minutes, 30 minutes and 60 minutes. Overall preference was also scored for each flavour (0-10 scale). The results are shown in FIGS. 5 through 8.

From this study we can conclude that Flavour 2 mod with the Evercool 190/180 combination was the preferred flavour overall and gave the best cooling after 5 minutes and the best long lasting freshness and tingling.

The invention claimed is:
1. A flavour composition comprising a mixture of coolant compounds comprising menthol in an amount of about 1% to less than 50% by weight of the total flavour composition and a menthane carboxamide consisting of a mixture of N-(4-cyanomethylphenyl) p-menthane carboxamide and 2-isopropyl-5-methyl-N-(2-(pyridin-2-yl)ethyl)cyclohexane carboxamide in an amount of 0.1% to 13% by weight of the total flavour composition.

2. The flavour composition according to claim 1, wherein the amount of menthol in the flavour composition is 5% to 30% by weight.

3. The flavour composition according to claim 1, wherein the total amount of menthane carboxamide in the flavour composition is about 0.1% to 10% by weight.

4. The flavour composition according to claim 1, wherein the total amount of menthane carboxamide in the flavour composition is 0.5% to 8% by weight.

5. The flavour composition according to claim 1, wherein said mixture of N-(4-cyanomethylphenyl) p-menthane carboxamide and 2-isopropyl-5-methyl-N-(2-(pyridin-2-yl)ethyl)cyclohexane carboxamide is provided in an amount of 1% to 9% by weight of the flavour composition.

6. The flavour composition according to claim 1, wherein the mixture of N-(4-cyanomethylphenyl) p-menthanecarboxamide and 2-isopropyl-5-methyl-N-(2-(pyridin-2-yl)ethyl)cyclohexane is provided in a ratio of 1:100 to 30:1.

7. The flavour composition according to claim 1, wherein the mixture of N-(4-cyanomethylphenyl) p-menthanecarboxamide and 2-isopropyl-5-methyl-N-(2-(pyridin-2-yl)ethyl)cyclohexane is provided in a ratio of 1:15 to 4:1.

8. A consumer product composition comprising a flavour composition as defined in claim 1.

9. The consumer product composition according to claim 8 that is an oral care product.

10. A method of compacting the amount of coolant employed in a flavour composition, comprising the step of adding to said flavour composition a mixture of menthol and menthane carboxamides as defined according to claim 1, wherein the coolant is menthol.

11. The consumer product composition according to claim 8, wherein the amount of menthol in the flavour composition is about 5% to 30% by weight, and wherein the total amount of menthane carboxamide in the flavour composition is about 0.1% to 10% by weight.

12. The consumer product composition according to claim 8, wherein the total amount of menthane carboxamide in the flavour composition is 0.5% to 8% by weight.

13. The consumer product composition according to claim 8, wherein the mixture of N-(4-cyanomethylphenyl) p-menthane carboxamide and 2-isopropyl-5-methyl-N-(2-(pyridin-2-yl)ethyl)cyclohexane carboxamide is provided in an amount of 1% to 9% by weight of the flavour composition.

14. The consumer product composition according to claim 8, wherein the mixture of N-(4-cyanomethylphenyl) p-menthanecarboxamide and 2-isopropyl-5-methyl-N-(2-(pyridin-2-yl)ethyl)cyclohexane carboxamide is provided in a ratio of 1:100 to 30:1.

15. The consumer product composition according to claim 8, wherein the mixture of N-(4-cyanomethylphenyl) p-menthanecarboxamide and 2-isopropyl-5-methyl-N-(2-(pyridin-2-ypethyl)cyclohexane carboxamide is provided in a ratio of 1:15 to 4:1.

16. The consumer product composition according to claim 9, wherein the amount of menthol in the flavour composition is about 5% to 30% by weight, and wherein the total amount of menthane carboxamide in the flavour composition is about 0.1% to 10% by weight.

17. The consumer product composition according to claim 9, wherein the total amount of menthane carboxamide in the flavour composition is 0.5% to 8% by weight.

18. The consumer product composition according to claim 9, wherein the mixture of N-(4-cyanomethylphenyl) p-menthane carboxamide and 2-isopropyl-5-methyl-N-(2-(pyridin-2-yl)ethyl)cyclohexane carboxamide is provided in an amount of 1% to 9% by weight of the flavour composition.

19. The consumer product composition according to claim 9, wherein the mixture of N-(4-cyanomethylphenyl) p-menthanecarboxamide and 2-isopropyl-5-methyl-N-(2-(pyridin-2-yl)ethyl)cyclohexane carboxamide is provided in a ratio of 1:100 to 30:1.

20. The consumer product composition according to claim 9, wherein the mixture of N-(4-cyanomethylphenyl) p-menthanecarboxamide and 2-isopropyl-5-methyl-N-(2-(pyridin-2-yl)ethyl)cyclohexane carboxamide is provided in a ratio of 1:15 to 4:1.

* * * * *